United States Patent [19]

Kaczmarek et al.

[11] 4,046,512

[45] Sept. 6, 1977

[54] DEVICE FOR INDICATING OVERHEATING IN GENERATORS

[75] Inventors: Thomas D. Kaczmarek; David C. Phillips, both of Penn Hills, Pa.

[73] Assignee: Westinghouse Electric Corporation, Pittsburgh, Pa.

[21] Appl. No.: 659,868

[22] Filed: Feb. 20, 1976

[51] Int. Cl.² ............... B01D 50/00; G01N 31/22
[52] U.S. Cl. .................. 23/253 TP; 23/232 R; 55/270; 55/483; 55/484
[58] Field of Search .......... 23/253 TP, 232 R, 254 R; 73/28; 55/270, 483, 484, 494, 487, DIG. 34

[56] References Cited

U.S. PATENT DOCUMENTS

| | | |
|---|---|---|
| 3,100,692 | 8/1963 | Wachter .................... 23/254 R |
| 3,693,327 | 9/1972 | Scheinberg .................... 23/254 R |
| 3,807,218 | 4/1974 | Carson et al. ................ 73/432 R X |
| 3,847,552 | 11/1974 | Hobgood et al. ............... 23/232 R |

*Primary Examiner*—Robert M. Reese
*Attorney, Agent, or Firm*—R. D. Fuerle

[57] ABSTRACT

The occurrence of excessively high temperatures in areas of a generator exposed to a cooling gas stream is visually indicated by passing a portion of the gas stream through an indicator device which comprises a filter holder containing a gas-permeable, particulate-collecting filter on which is an indicator which produces a visual effect when contacted by particulates. A valve controls the flow of the gas to the device and is opened by a monitor when the monitor detects particulates in the gas stream.

7 Claims, 3 Drawing Figures

DEVICE FOR INDICATING OVERHEATING IN GENERATORS

CROSS-REFERENCE TO RELATED APPLICATION

This application is related to application Ser. No. 426,391, filed Dec. 19, 1973, now U.S. Pat. No. 3,972,225, by E. M. Fort, T. D. Kaczmarek, and D. C. Phillips, titled "Sampling System For Power Generators." That application describes a system for monitoring the gas stream of generator and automatically taking a sample of it when it contains particulates.

BACKGROUND OF THE INVENTION

Large electrical generators are cooled by a gas stream that flows througout the generator. when a malfunction occurs the particular area involved will overheat. Organic materials in the overheated area are affected first and degrade, producing particulates (i.e., "thermoparticulate") which enter the gas stream. Special compounds can be placed throughout the generator which thermoparticulate at much lower temperatures than most organic materials used in the generator.

A portion of the gas stream is diverted to a monitor which detects the presence of particulates in the gas stream and sounds an alarm. It may also open a valve so that a portion of the gas stream passes through a filter which collects a sample of the particulates. The sample is analyzed to determine which of the thermoparticulating compounds placed throughout the generator has degraded, thus pinpointing the area of malfunction. A better decision can then be made as to whether to reduce the load on the generator or shut it down, and if the latter, repair time is greatly reduced since one knows where to look.

Collecting samples and analyzing them requires a certain amount of time, but when the alarm goes off a decision must be made immediately at least as to whether or not to reduce the load on the generator. Failure to reduce the load should a true emergency exist may mean extensive damage to the generator. On the other hand, any reduction in load constitutes an immediate loss of electricity generated. The operator may be reluctant to base such a weighty decision on an unconfirmed alarm from a single monitor.

PRIOR ART

U.S. Pat. No. 3,689,224 (column 4, lines 50–52) describes glass filters coated with silica gel for gas analysis.

U.S. Pat. Nos. 1,321,062, 2,487,077, and 2,736,638 disclose various gas detectors which show the presence of a gas by the color change of an indicator. The indicator is placed on various materials in tubes which are sealed and opened to admit the gas to be tested.

SUMMARY OF THE INVENTION

We have found that overheating in areas of a generator exposed to the generator's cooling gas stream can be visually indicated by passing a portion of the gas stream through a gas-permeable, particulate-collecting filter on which is placed an indicator which produces a visual effect in the presence of particulates. The passage of the gas stream through the filter can be controlled by a monitor which permits passage when particulates are detected in the gas stream.

This invention permits the operator of a generator to confirm an alarm signal from the monitor by a visual effect on the filter. Moreover, because the filter may have several separate areas each containing a different indicator, which indicates only the presence of particulates from particular thermoparticulating compounds placed throughout the generator, the operator is also provided with information as to where in the generator the overheating is occurring, which is very useful in deciding whether to reduce the load, and if so, by how much, or to shut down the generator.

DESCRIPTION OF THE INVENTION

DESCRIPTION OF THE PREFERRED EMBODIMENT

Figure 1:
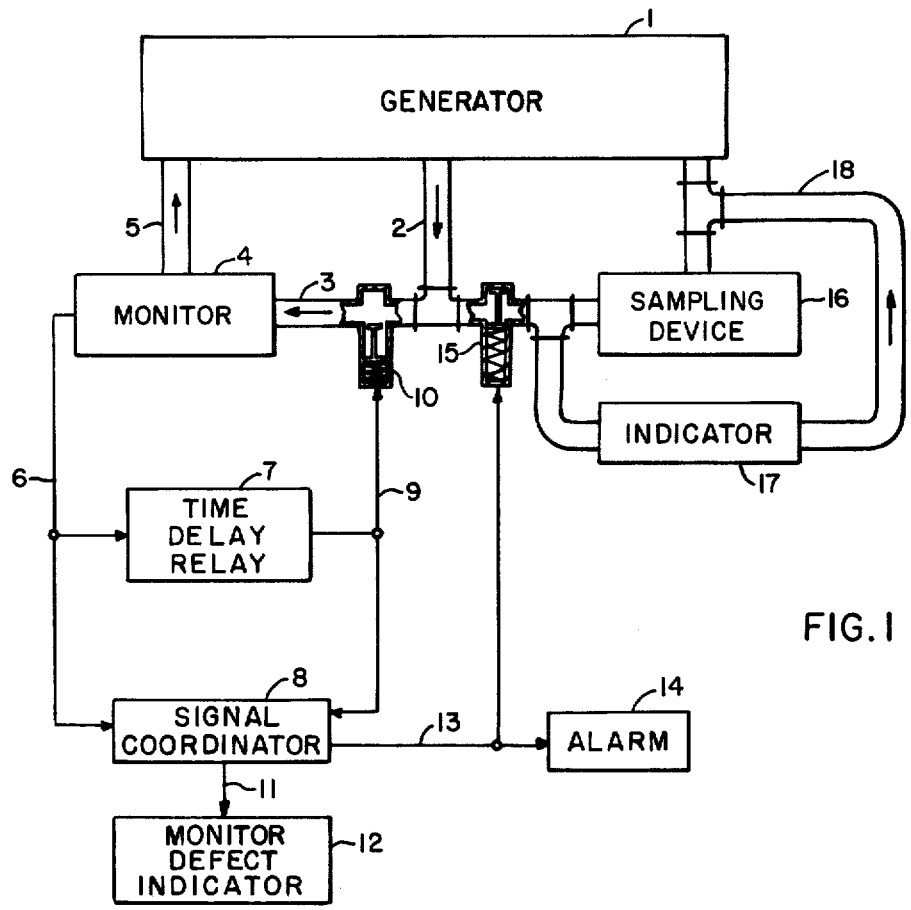
FIG. 1 is a diagram which shows a presently preferred relationship between the indicator device, the monitor, and the generator.

In FIG. 1, a generator 1 is cooled by a gas stream, usually of hydrogen, a portion of which passes through conduits 2 and 3, through monitor 4, then through conduit 5 back to the generator. When the monitor detects the presence of particulates in the gas stream, a signal is sent in line 6 to time delay relay 7 and to signal coordinator 8. Since insulation falling off and other debris can set off the monitor, the time delay relay ignores all signals from the monitor unless the signal is continuous over a pre-set length of time. If a continuous signal is received the time delay relay sends a signal through line 9 to signal blocker 10 and to signal coordinator 8. Since the signal may be due to a malfunction in the monitor, signal blocker 10 either blocks the flow of gas to the monitor or filters the particulates out of it. If the signal from the monitor then ceases, it is assumed that the monitor is functioning properly. If signal coordinator 8 receives a signal in line 9 which is not followed by a cessation of the signal in line 6 it sends a signal in line 11 to monitor defect indicator 12. Otherwise, it sends a signal in line 13 to alarm 14 and to valve 15. Valve 15 opens letting the gas stream pass through sampling device 16, which collects a sample of the particulates, and through indicator device 17 which provides a visual effect if particulates are present in the gas stream. The gas then passes through conduit 18 back to the generator. Gas flow through sampling device 16 and indicator device 17 are independently controlled.

Figure 3:
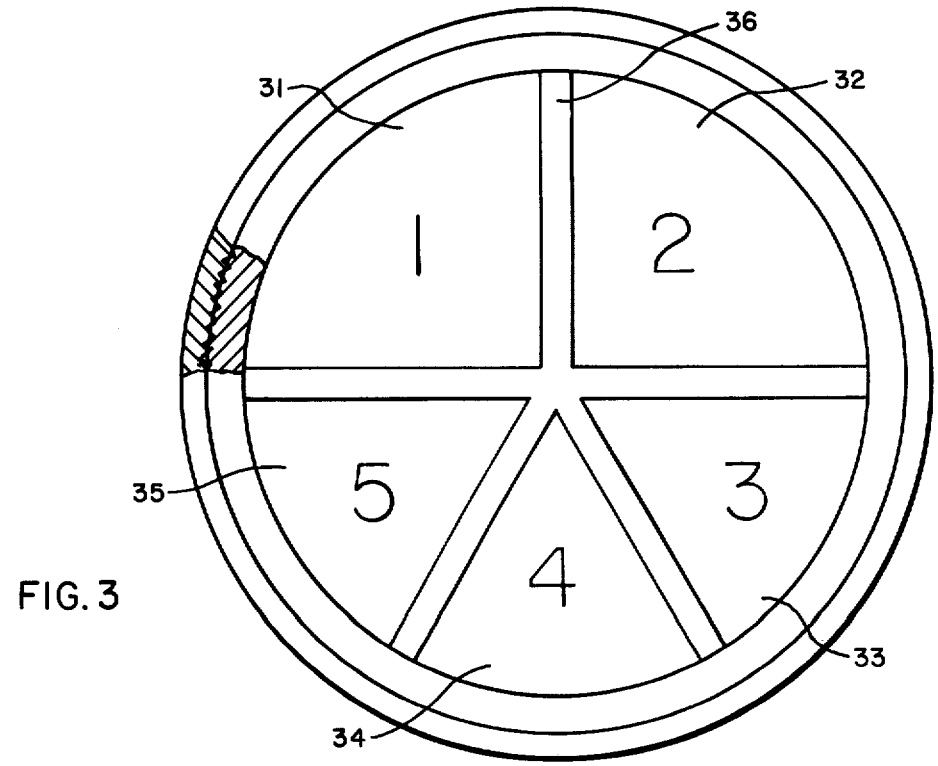
FIG. 3 is a view through III—III in FIG. 2 and shows a presently preferred embodiment of a particulate-collecting filter according to this invention.
Figure 2:
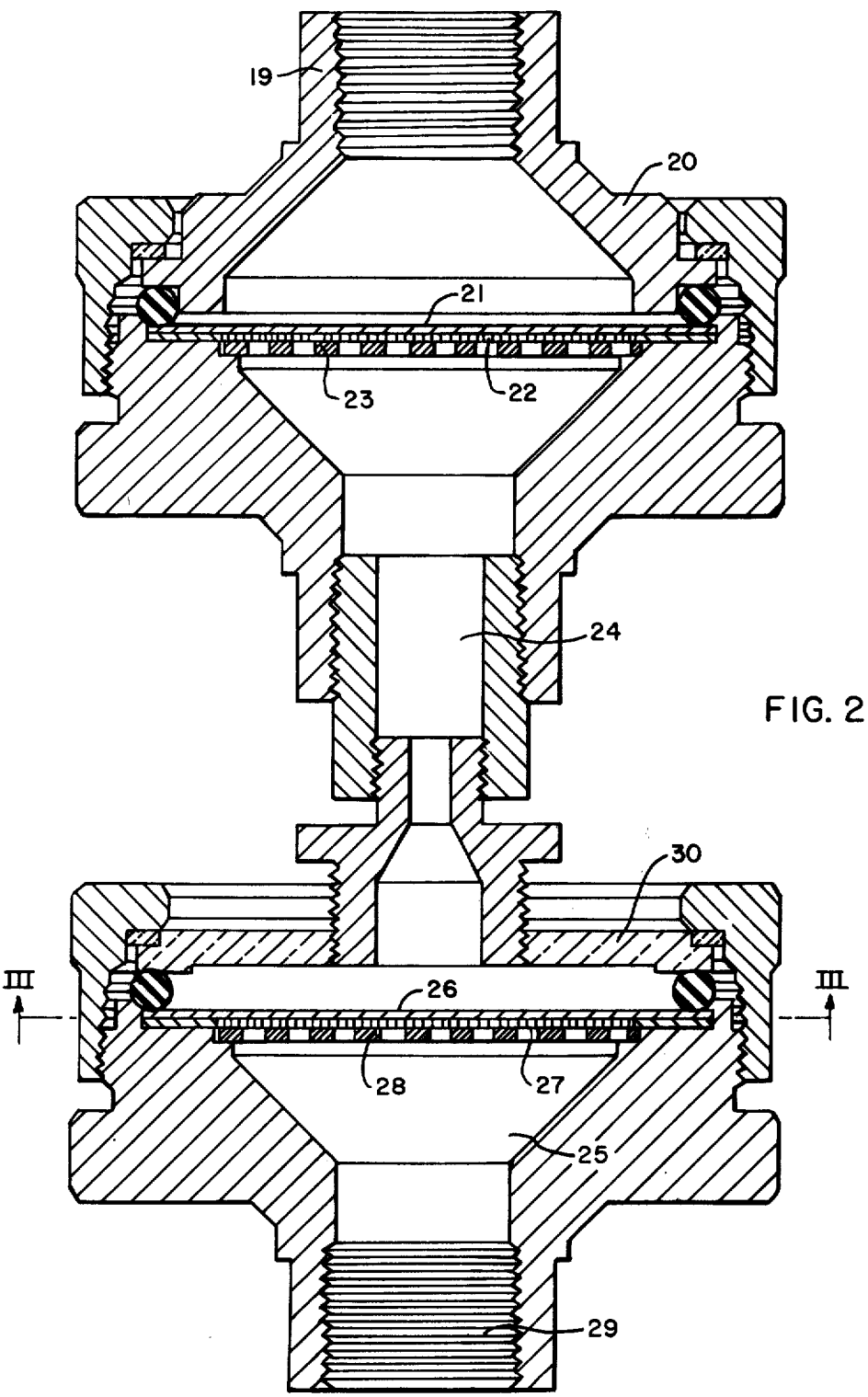
FIG. 2 is a cross-sectional view of a presently preferred indicator device according to this invention.

FIGS. 2 and 3 show more detail of this indicator device. In FIG. 2 gas enters stem 19 and passes to chamber 20. This chamber holds a filter 21 supported by fine screen 22 and wire mesh 23. This filter removes large (e.g., > 10 micron) particles from the gas stream. These large particles are not the small particulates produced by thermoparticulation and therefore are not very useful in determining if overheating has begun. They are removed, however, so that they do not foul up the particulate filter and give spurious results. The gas then passes through channel 24 to chamber 25 which holds particulate filter 26, also supported by a fine screen 27 and wire mesh 28, before exiting through channel 29. Chamber 25 is preferably provided with a window 30 so that the filter can be observed without disassembling the device.

Referring to FIG. 3, a plan view of a particulate filter is shown, which is divided into five areas 31, 32, 33, 34, and 35. Preferably, each area has on its surface a different indicator, but some areas may be left blank or more than one area may have the same indicator if all of the areas are not needed. The areas need not be the same size as some indicators may require more surface. While the pie-shaped design shown in FIG. 3 is preferred because each area is subjected to both the center and edges of the gas stream, other designs such as stripes or concentric circles could also be used. One to six areas are preferred, as that is usually adequate for the number of different thermoparticulating compounds in a generator. The areas are preferably separated from each other by an impermeable material (36 in FIG. 3) such as wax or polyethylene to prevent the intermixing of the indicators. The indentification of the areas can be made by making them of different sizes or by imprinting a number on them or both as shown in FIG. 3. Separate filters in parallel could also be used but would be more expensive.

The particulate filter material must be gas-permeable, yet fine enough to collect particulates on its surface. Suitable materials include glass and paper; glass is preferred as it is more inert.

The indicator must produce a visual effect when contacted by particulates. An indicator which indicates vapors but not particulates is not suitable because the residence time on the filter of vapors is not long enough for a good reaction and because vapors are not as useful as a symptom of overheating. The visual effect may be a change from one color to another, from colorless to colored or vice-versa, from opaque to clear or vice-versa, or some other observable difference. Since some of the thermoparticulating compounds, such as malonic acid and its derivatives, produce acidic particulates, indicators which change color in the presence of acid are often useful. The examples given hereinafter illustrate various combinations of indicators and thermoparticulating compounds.

If the indicator is solid, the particulate filter can usually be prepared by simply dissolving the indicator in a solvent, depositing the solution on the filter material, and evaporating the solvent. Some filter materials, however, must be activated. Generally, this is accomplished by dipping the filter material in potassium silicate solution, perfusing with carbon dioxide, washing with ammonium chloride, then clean water, and heating at about 90° C, to provide an active silica gel coating on the filter material. Details are provided in U.S. Pat. No. 3,689,224.

The following examples further illustrate this invention.

EXAMPLES

The apparatus used for testing the indicator device is designed to simulate turbine generator conditions. Hydrogen (7 l/min flow rate) was passed over the samples which were contained in a stainless steel boat within a stainless steel tube (1 inch o.d.). Accurate temperature measurements were made by mounting the hot-junction of a Chromel-Alumel thermocouple within a small hole in the boat. A phase controlled temperature regulator and programmer acted as a temperature control on the furnace. The output of the thermocouple and detector was monitored on a two pen potentiostatic recorder. A 5° C/min heating rate was maintained in each experiment after the insertion of the sample in the boat. When the "alarm" or threshold temperature (temperature at which considerable particulation occurred; usually ~ 0.1–0.3 mA on both the Environment One Generator Condition Monitor and G.E. Core Monitor) was reached, the hydrogen stream to the detector was by-passed through the indicator device. In some instances, the hydrogen stream was concurrently allowed to pass through the monitor and particulate indicator device. The table shows the results obtained with various common insulating resins and with certain special compounds that thermoparticulate at lower temperatures than do the insulating resins.

TABLE I

| Thermoparticulating Compound | Indicator | Color Change | Temperature Of Thermoparticulating Compound When Color Change Occurred (° C) |
|---|---|---|---|
| Epoxy resin | methyl cellulose in 50% $H_2SO_4$ | colorless to pink* | 246 |
| Phenolic resin | methyl cellulose in 50% $H_2SO_4$ | colorless to pink* | 224 |
| Malonic acid | bromocresol green | blue to yellow | 120 |
| " | 2-(paradimethylaminophenylazo)-pyridine | beige to pink | 120 |
| " | methyl red | yellow to red | 112 |
| " | methyl purple | green to purple | 120 |
| " | 4(4-dimethylamino-1-naphylazo)-3 methoxy benzene sulfonic acid | yellow to violet | 120 |

*In both instances, the color intensified to a dark red on further heating.

The test method can be best described by considering the use of methyl red as the impregnant in conjunction with heating a malonic acid sacrificial compound. Upon alarm of Generator Condition Monitor at 112° C, the total hydrogen effluent was passed through a glass fiber disc (contained in indicator device) and impregnated with methyl red indicator solution. The heating rate was maintained at 5° C/min; after only 15 seconds, a pink coloration of the disc was discernible which changed to a dark red color after 2½ minutes.

Hence, if this disc had been employed in the field, a confirmation of the Generator Condition Monitor alarm could be made within minutes of alarm at the generator site (i.e., the time consuming shipping of effluent sample for laboratory analysis could be avoided and a course of action could be taken immediately by the utility concerned).

It should be noted that in examples concerning the heating of the epoxy and phenolic resins, the temperatures associated with disc color change are 246° and 224° C, respectively. Thermoparticulation temperatures (and hence the temperature at which the Generator Condition Monitor signals alarm) for these resins are 261° and 268° C, respectively. Hence, by the use of the indicator device of this invention, an earlier indication of thermal stress is signaled by the color change; this may permit an earlier generator shutdown and less insulation damage.

We claim:
1. In combination,
   A. a generator having a cooling gas stream passing therethrough;
   B. an indicator device for indicating the presence of particulates in said gas stream comprising
      1. a filter holder having a gas inlet and a gas outlet, connected so that at least a portion of said cooling gas stream can pass therethrough;
      2. a gas-permeable, particulate-collecting filter within said filter holder, the surface of said filter which faces said gas inlet being divided into at least two areas; and
      3. at least two different chemical indicators, each on a different area of said filter, each chemical indicator producing a visual effect when contacted by particulates; and
   C. a valve between said generator and said cooling gas stream for controlling its flow through said indicator device, whereby particulates in said gas stream can collect on said filter producing a visual effect.

2. A combination according to claim 1 wherein said filter holder is provided with a window whereby said visual effect can be observed without disassembling said device.

3. A combination according to claim 1 wherein said areas are separated from each other by an indicator impermeable barrier.

4. A combination according to claim 1 wherein said areas are pie-shaped.

5. A combination according to claim 1 wherein the number of said areas is 2 to 6.

6. A combination according to claim 1 including a monitor, which monitors said gas stream for the presence of particulates therein and opens said valve when said particulates are detected.

7. A combination according to claim 1 including a second filter which removes particles larger than 10µm from said gas stream before said gas stream passes through said particulate-collecting filter.

* * * * *